United States Patent
Cabeza-Guillen et al.

(10) Patent No.: US 9,971,172 B2
(45) Date of Patent: May 15, 2018

(54) METHOD FOR DETERMINING THE FAR VISUAL POINT FOR A SPECTACLE LENS AND SYSTEM THEREFOR

(71) Applicant: Carl Zeiss Vision International GmbH, Aalen (DE)

(72) Inventors: Jesus-Miguel Cabeza-Guillen, Aalen (DE); Subhashini Mani, Waiblingen (DE); Michael Gamperling, Leipheim (DE)

(73) Assignee: Carl Zeiss Vision International GmbH, Aalen (DE)

( * ) Notice: Subject to any disclaimer, the term of this patent is extended or adjusted under 35 U.S.C. 154(b) by 11 days.

(21) Appl. No.: 15/274,151

(22) Filed: Sep. 23, 2016

(65) Prior Publication Data
US 2017/0038608 A1 Feb. 9, 2017

Related U.S. Application Data

(63) Continuation-in-part of application No. 15/212,060, filed on Jul. 15, 2016, which is a continuation of application No. PCT/EP2015/050554, filed on Jan. 14, 2015.

(30) Foreign Application Priority Data

Jan. 15, 2014 (DE) .................. 10 2014 200 637
Jul. 20, 2016 (DE) .................. 10 2016 113 374

(51) Int. Cl.
G02C 13/00 (2006.01)
A61B 3/00 (2006.01)
A61B 3/11 (2006.01)

(52) U.S. Cl.
CPC .......... *G02C 13/005* (2013.01); *A61B 3/0025* (2013.01); *A61B 3/111* (2013.01)

(58) Field of Classification Search
CPC ...... G02C 13/005; A61B 3/0025; A61B 3/111
USPC ............................................... 359/204
See application file for complete search history.

(56) References Cited

U.S. PATENT DOCUMENTS

| | | |
|---|---|---|
| 6,659,609 B2 | 12/2003 | Mothes |
| 7,588,335 B2 | 9/2009 | Kubitza |
| 7,950,800 B2 | 5/2011 | Nauche et al. |
| 2009/0214086 A1 | 8/2009 | Thomet |
| 2010/0128220 A1 | 5/2010 | Chauveau |
| 2010/0195045 A1 | 8/2010 | Nauche et al. |

(Continued)

OTHER PUBLICATIONS

Translation and Office action of the German Patent Office dated Jun. 1, 2017 in German patent application 10 2016 113 374.4 on which a claim of priority is based.

(Continued)

*Primary Examiner* — Zachary Wilkes
*Assistant Examiner* — Mitchell Oestreich
(74) *Attorney, Agent, or Firm* — Walter Ottesen, P.A.

(57) ABSTRACT

The invention is directed to a method allowing the exact determination of the far visual point on spectacle lenses in a spectacle frame for a subject while taking into account the habitual head position or body posture. The method renders it possible to specify the coordinates of the far visual point on spectacle lenses in a coordinate system that is fixed in relation to the spectacle frame coordinate system. The invention also relates to a system carrying out the method.

16 Claims, 4 Drawing Sheets

(56) References Cited

U.S. PATENT DOCUMENTS

2013/0188128 A1* 7/2013 Divo .................... G02C 13/005
                                                        351/204
2014/0240664 A1    8/2014 Divo et al.

OTHER PUBLICATIONS

International Search Report dated May 4, 2015 of international application PCT/EP2015/050554 on which this application is based.
DIN EN ISO 13666, "Opthalmic optics—Spectacle lenses—Vocabulary (ISO 13666:2012)", DIN Deutsches Institut fuer Normung, e.V., 114 pages, Oct. 2013.

* cited by examiner

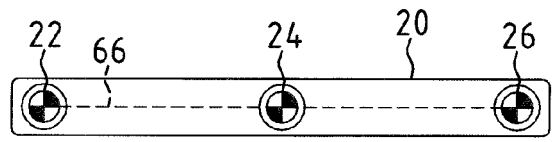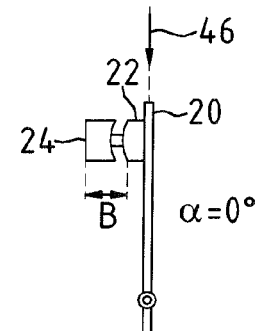
FIG. 5A        FIG. 5B
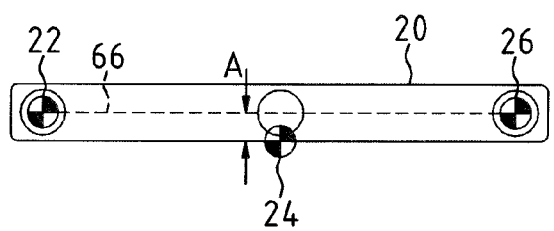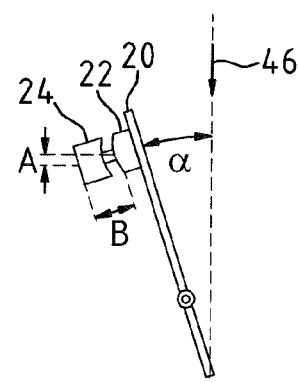
FIG. 6A        FIG. 6B
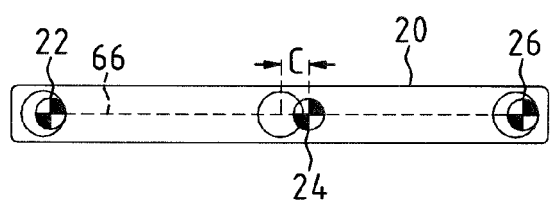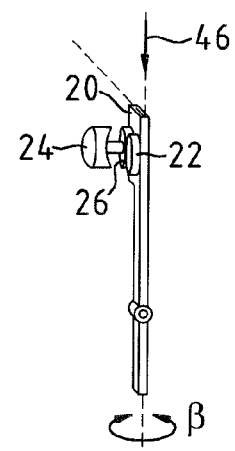
FIG. 7A        FIG. 7B

US 9,971,172 B2

METHOD FOR DETERMINING THE FAR VISUAL POINT FOR A SPECTACLE LENS AND SYSTEM THEREFOR

CROSS REFERENCE TO RELATED APPLICATIONS

This application claims priority from German patent application 10 2016 113 374.4, filed Jul. 20, 2016 and is a continuation-in-part application claiming priority from patent application Ser. No. 15/212,060, filed Jul. 15, 2016, which, in turn, claims priority from international patent application PCT/EP2015/050554, filed Jan. 14, 2015, which designates the U.S. and claims priority from German patent application 10 2014 200 637.6, filed Jan. 15, 2014. The present continuation-in-part application claims priority to each of the above applications and incorporates herein the entire contents thereof by reference.

FIELD OF THE INVENTION

The invention relates to a method for determining a far visual point on a spectacle lens which is receivable in a spectacle frame and which has a frame plane, in which an image, lying in an image plane, of at least one portion of a spectacle frame worn by a subject is acquired by a camera with an optical axis while the subject looks into the camera with a viewing direction of at least one eye passing through the frame plane, in which a pantoscopic angle $\alpha'$ of the spectacle frame related to the position of the image plane is established, the pantoscopic angle being corrected in accordance with the acquired inclination angle $\gamma$ of the image plane in relation to the vertical direction so as to form a pantoscopic angle $\alpha$ related to the vertical direction, in which a head rotation angle $\beta$ of the head of the subject, formed by the optical axis of the camera with a plane perpendicular to the distance line of the pupils of the eyes of the subject, is established, in which the head rotation angle $\beta$ is corrected in accordance with the detected inclination angle $\gamma$ of the image plane in relation to the vertical direction so as to form a corrected head rotation angle $\beta$ corresponding to a horizontal alignment of the optical axis of the camera, and in which the distance visual point is determined by analyzing the image lying in the image plane, taking into account the corrected head rotation angle $\beta'$ corresponding to a horizontal alignment of the optical axis of the camera. Moreover, the invention also relates to a system for determining such a far visual point and to a computer program.

BACKGROUND OF THE INVENTION

WO 2015/107063 A1 has disclosed such a method and system, and such a computer program.

In order to fit the spectacle lenses correctly into a spectacle frame, it is necessary to determine so-called fitting parameters so that the optical centers of the lenses can be made to coincide with the visual axes of the corresponding eyes in order thus, for example, to know information about the interpupillary distance and the information about the level of the pupils in relation to the spectacle frame. Moreover, it is important to determine the level of the optical centers of the spectacle lenses in relation to the upper or lower edge of the spectacle frame, into which the spectacle lenses are inserted.

By way of example, fitting parameters can be determined by virtue of an optician and a subject sitting or standing opposite one another, with the subject wearing the frame of his choice with a support lens held therein. The subject is asked to look into the distance and the optician then indicates the visual point with a cross on the lens or on a contact line foil according to appearance, as identified when looking at one another. This cross (centering cross) then determines the position of the optical center of the spectacle lens to be inserted into the frame. This method is carried out individually for each eye of a subject. The distance between the centering crosses established in this manner is the interpupillary distance PD.

U.S. Pat. No. 6,659,609 has described a system for determining fitting parameters for spectacle lenses which contains a digital camera accommodated on a column in a height-adjustable manner, the lens of which camera being arranged in the region of the front surface of the housing, together with a mirror and a light source. This system comprises a computer linked to the digital video camera, the computer determining fitting parameters for the spectacle frame by image evaluation of the image of a subject with a spectacle frame and a measurement bracket fastened to the spectacle frame. For the purposes of determining the fitting parameters, the subject is asked in this case to look directly into the digital camera, with the optical axis of the camera having to be parallel with the viewing direction of the subject. As an alternative thereto, provision can also be made for displacing the camera in order to ensure that the image plane of the camera is parallel with the plane of the measurement frame and the image of the eyes of the subject is then centered in the image plane of the camera in relation to the optical axis thereof.

United States patent application publication 2010/0195045 A1 has described a method for determining spectacle lens fitting parameters, in which the sought-after fitting parameter is determined by means of image analysis from the image of a subject wearing spectacles with a measurement bracket fixed thereon, which image was acquired by a camera. In this case, the subject is asked to look at an LED attached to the camera. The camera contains an inclination sensor in order thereby to determine the inclination angle of the optical axis of the camera in relation to the horizontal. The camera emits a warning signal if the inclination angle acquired by means of the inclination sensor exceeds a threshold. This ensures that the optical axis of the camera always intersects the frame plane of the spectacle frame approximately perpendicularly during the image recording. What this achieves is that a parallax error caused by the distance of the eyes of the subject from the frame plane is negligible when determining fitting parameters. In the case where the frame plane is not parallel to the image plane of the camera, United States patent application publication 2010/0195045 A1 proposes a computational image correction in order thereby to compensate an image distortion caused by this recording situation.

SUMMARY OF THE INVENTION

It is an object of the invention to allow the exact determination of the far visual point on spectacle lenses in a spectacle frame for a subject, taking into account the habitual head position or body posture.

The invention renders it possible, in particular, to specify the coordinates of the far visual point on spectacle lenses in a coordinate system that is fixed in relation to the spectacle frame, that is, in a frame coordinate system.

The invention is based on the idea that, in order to establish the fitting parameters for spectacle lenses in a spectacle frame by analyzing images of a spectacle frame put on by a subject, it is not absolutely necessary to use a camera securely installed in the room but that these fitting parameters can, in principle, also be established by virtue of images taken by a hand-held camera which, for example, is integrated into a tablet computer being evaluated. However, the inventors have recognized that the fitting parameters established in this way often deviate from the fitting parameters which are determined by analyzing corresponding images which are acquired by a camera securely installed in the room, as is described, for example, in U.S. Pat. No. 6,659,609.

In comprehensive trials, the inventors determined that the inclination angle of the image plane of the camera in relation to the vertical direction when recording the images is decisive for the error which may occur when determining spectacle lens fitting parameters for spectacle lenses, which should be accommodated in a spectacle frame, by analyzing images of the spectacle lens put on by a subject if the corresponding images are recorded by a camera which is not securely installed but is held in the hands.

In particular, the inventors determined that the influence of the inclination angle of the image plane of the camera in relation to the vertical direction cannot be readily compensated by means of image evaluation, unlike the tilt of the camera about the optical axis of a camera lens system or the swiveling of the camera about an axis extending in the vertical direction.

Thus, an idea of the invention is, in particular, to acquire the inclination of the camera image plane in relation to the vertical direction by an inclination sensor, as is routinely integrated in tablet computers with a camera or in smartphones with a camera, such as, for example, the iPad® or the iPhone®, and then to take this into account together with the position of at least one reference point, arranged on the subject, relative to the spectacle frame and/or the camera image plane when determining the far visual point and further parameters for spectacle lenses by image evaluation of images of a spectacle frame which was provided with a measurement bracket and put on by a subject.

That is, if, for example, a tablet computer is not held precisely vertically during the recording, the pantoscopic angle $\alpha$ for spectacle lenses in the spectacle frame, as observed by the camera, deviates from the actual pantoscopic angle $\alpha$ of these spectacle lenses, and so very large errors may occur, for example, when calculating centration data by image evaluation from such recordings. The calculated centration data, in particular the visual point height of the subject through the spectacle lens, are generally associated with errors and depend on how the subject orients his or her head in relation to the camera, that is, both on how far he or she raises or lowers the head in relation to the camera and how far he or she rotates the head relative to the camera.

Therefore, in order to determine a distance visual point on a spectacle lens which is receivable in a spectacle frame and which has a frame plane, the invention proposes that an image, lying in an image plane, of at least one portion of a spectacle frame worn by a subject is acquired by a camera with an optical axis while the subject looks into the camera with a viewing direction of at least one eye passing through the frame plane. In the method according to the invention, a pantoscopic angle $\alpha'$ of the spectacle frame related to the position of the image plane is established, the pantoscopic angle being corrected in accordance with the acquired inclination angle $\gamma$ of the image plane in relation to the vertical direction so as to form a pantoscopic angle $\alpha$ related to the vertical direction. In the method according to the invention, a head rotation angle $\beta$ of the head of the subject, formed by the optical axis of the camera with a plane perpendicular to the distance line of the pupils of the eyes of the subject, is also established. Moreover, in the method according to the invention, the head rotation angle $\beta$ is corrected in accordance with the detected inclination angle $\gamma$ of the image plane in relation to the vertical direction so as to form a corrected head rotation angle $\beta'$ corresponding to a horizontal alignment of the optical axis of the camera and the distance visual point is determined by analyzing the image lying in the image plane, taking into account the corrected head rotation angle $\beta'$ corresponding to a horizontal alignment of the optical axis of the camera. The intersection of the viewing direction with the frame plane is then determined by means of image evaluation.

Here, the distance visual point is determined as the intersection of a virtual viewing direction lying in a horizontal plane with the frame plane, the intersection of the viewing direction with the frame plane being determined by means of image evaluation, and wherein the virtual viewing direction is determined as the direction of a virtual straight line, which is established by rotating a straight line which is set by a reference point arranged on the eye with a known position in relation to the camera or the spectacle frame and the intersection of the viewing direction. For this, this straight line is, firstly, rotated at a virtual pivot, which lies at a distance from the reference point and on this straight line within the eye, about an axis lying parallel to the vertical direction by a first angle ($\beta_{OD}"$, $\beta_{OS}"$) dependent on the corrected head rotation angle ($\beta'$). Secondly, this straight line is rotated at the virtual pivot about a further axis by a further angle ($\alpha"$) dependent on the corrected pantoscopic angle ($\alpha$). This further axis is parallel to the distance line of the pupils of the eyes of the subject.

If the eye is a right eye of the subject, the following applies for the first angle ($\beta_{OD}"$) which is dependent on the corrected head rotation angle ($\beta'$): $\tan \beta_{OD}\theta = (0.5 \times P_D \times \cos \beta' + YZ)/(D\alpha HSA)$, and if the eye 62 is a left eye of the subject 68, the following applies: $\tan \beta_{OS}" = (0.5 \times P_D \times \cos \beta' - YZ)/(D + HSA)$.

Here, $P_D$ is the interpupillary distance of the eyes of the subject, where D+HSA is the vertical distance of the camera from a vertical plane, in which the distance line of the pupils of the eyes is situated, and where YZ is the offset of the intersection (Y) of the distance line of the pupils of the eyes with the vertical projection of the optical axis of the camera into a horizontal plane, in which the distance line of the pupils of the eyes is situated, from the intersection (Z) of the distance line of the pupils of the eyes with a vertical plane intersecting the distance line of the pupils of the eyes, the plane being perpendicular to the frame plane and the vertical axis of symmetry of the spectacle frame lying in the plane. Here, in the present case, the perpendicular projection of a straight line or of an axis into a plane is understood to be a projection of the axis or the straight line into the plane in a direction which is perpendicular to the plane. The following applies for the further angle ($\alpha"$) dependent on the corrected pantoscopic angle ($\alpha$): $\alpha" = -(\gamma + \delta)$, where $\delta$ is the angle which the optical axis of the camera forms with the perpendicular projection of the viewing direction into a vertical plane, in which the optical axis of the camera lies.

The invention renders possible determining at least one fitting parameter by virtue of, initially, a distance visual point being determined and then, the at least one fitting parameter being determined from the distance visual point and from the acquired image by means of image evaluation.

What the invention achieves is that it is possible, when determining the fitting parameters, to take into account a parallax error caused by the offset of the eyes of the subject from the spectacle frame and hence, in particular, the habitual head position of the subject. The fitting parameters established with the aid of the method according to the invention can then, in particular, reflect the fact that the leading eye of a subject, when observing an object, can face the object while the other eye of the subject is positioned in a recessed manner relative to the object in relation to the leading eye.

It is not necessary for the camera to be held in a specific position or orientation to determine the distance visual point and also further fitting parameters using the method according to the invention. Rather, it is sufficient if the camera acquires the face of the subject with the spectacle frame worn by the subject in such a way that the image of the subject contains at least the pupil of one of the eyes, preferably the pupils of both eyes, and, moreover, those portions of the spectacle frame which render it possible to establish the relative position of the spectacle frame in relation to the image plane of the camera by means of image evaluation of the image acquired by the camera in the case of a known geometry of the spectacle frame.

The pantoscopic angle $\alpha'$ of the spectacle frame related to the position of the image plane can then be established, for example, by means of image analysis of the acquired image of the at least one portion of the spectacle frame worn by the subject. In particular, it is possible that the head rotation angle $\beta$ of the head of the subject, formed by the optical axis of the camera with a plane perpendicular to the distance line of the pupils of the eyes of the subject, is established by means of image analysis of the acquired image of the at least one portion of the spectacle frame worn by the subject.

However, it is possible to determine the distance visual point and also further fitting parameters particularly exactly by virtue of the image lying in the image plane being acquired together with at least three front target marks which are fixed in relation to the spectacle frame, wherein at least one of the front target marks is arranged spatially offset perpendicular to the front side in relation to the at least two other front target marks. By way of example, these front target marks can be formed on a measurement bracket which is fastened to the spectacle frame. Then, the three front target marks arranged on the front side of the measurement bracket define a spatial coordinate system.

Preferably, $\alpha=\alpha'\gamma$ applies for the corrected pantoscopic angle and $\beta=\beta/\cos(\alpha'-\gamma)$ applies for the corrected head rotation angle.

Advantageously, the image of the spectacle frame is acquired by a digital camera in the method according to the invention, the camera containing an inclination sensor acquiring the inclination of the image plane Y about a horizontal axis.

By way of example, this inclination sensor can be a gravity sensor which establishes the direction of gravity. As an alternative thereto, the inclination sensor can also be embodied as a sensor which evaluates the direction of the Earth's magnetic field. In particular, the inclination sensor can also be a sensor evaluating both the direction of the Earth's magnetic field and the direction of gravity, for example, a combined gravity/magnetic field sensor.

Here, the image of the portion of the spectacle frame worn by the subject can be acquired, for example, if a measurement bracket is connected to the spectacle frame, the measurement bracket having a front side with at least three front target marks for measuring the pantoscopic angle $\alpha$ of the spectacle frame to be measured, wherein at least one of the front target marks is arranged spatially offset perpendicular to the front side of the measurement bracket in relation to the at least two other front target marks.

Thus, from an image of at least one portion of the spectacle frame worn by the subject and the distance visual point determined therewith, it is possible, for example, to determine, as fitting parameter, the frame dimensions (I, h, AzG [distance between lenses]), the interpupillary distance ($P_D$, $z_R$, $z_L$), the centration distance ($x_R$, $y_R$, $x_L$, $y_L$), the pantoscopic tilt, the face form angle and/or the required lens blank diameter.

The reference point is preferably the corneal vertex of the eye of the subject. By way of example, the corneal vertex can be determined by way of a reflection-based centration. However, it is also possible for the reference point to be a center of the pupil of the eye of the subject. By way of example, this center of the pupil can be established by means of image processing on a computer or it can be determined by an operator, for example, an optician, in an image of the eyes of the subject.

The known position of the at least one reference point arranged on the subject in the coordinate system defined by the at least three front target marks which are fixed in relation to the spectacle frame can, for example, be established by analyzing an image of the subject from the side, for example, an image of the subject who is wearing a measurement bracket with three target marks, arranged in each case at the two sides of the measurement bracket, for determining the vertex distance and face form angle, as is described in U.S. Pat. No. 7,588,335, to which reference is made in respect of the entirety thereof and the disclosure of which is incorporated in the disclosure of this application. In particular, the analyzed image of the subject can be an image of the subject from the side which was acquired by the camera. The target marks arranged at the two sides of the measurement bracket are then attached at an angle of essentially 90° in relation to the front target marks. They enable the calibration of an image of the subject from the side and therefore allow the vertex distance to be measured on the basis of such an image.

However, it should be noted that the vertex distance (HSA) can also be determined by measuring the subject by means of a so-called PD ruler in order then to take it into account as a known position of the at least one reference point arranged on the subject in the coordinate system defined by the at least three fixed front target marks defined in relation to the spectacle frame in the method according to the invention for determining at least one fitting parameter for a spectacle lens which is receivable in a spectacle frame. It should be noted that, in the method according to the invention, the vertex distance can also be read from a database as a mean value for a multiplicity of subjects. In particular, it should be noted that this mean value may be, for example, a mean value for the vertex distance of a certain population of subjects or certain sub-groups of a population of subjects.

The position of the virtual pivot on the straight line fixed by the reference point with the known position in relation to the camera or the spectacle frame and the point of intersection of the viewing direction can be determined, for example, by predetermining a fixed distance (A) of the virtual pivot from the reference point. The interpupillary distance $P_D$ of the eyes of the subject can be established, for example, by means of image analysis of an image acquired by the camera, the image containing the pupils of the eyes of the subject and at least one portion of the spectacle frame worn by the subject. The angle ($\delta$) which the optical axis of the camera forms with the perpendicular projection of the viewing direction in a vertical plane can be established, for example by means of image analysis of the acquired image of the at least one portion of the spectacle frame worn by the subject.

The offset of the intersection (Y) of the distance line of the pupils of the eyes with the perpendicular projection of the optical axis of the camera in a horizontal plane, in which the distance line of the pupils of the eyes is situated, from the intersection (Z) of the distance line of the pupils of the eyes with a vertical plane which intersects the distance line of the pupils of the eyes and which is perpendicular to the frame plane, the vertical axis of symmetry of the spectacle frame lying in the vertical plane, can likewise be established by means of image analysis of an image acquired by the camera, the image containing the pupils of the eyes of the subject and at least one portion of the spectacle frame worn by the subject.

A system according to the invention for determining a distance visual point on a spectacle lens which is receivable in a spectacle frame and which has a frame plane contains a camera, having an image plane, comprising an inclination sensor detecting the inclination of the image plane of the camera about a horizontal axis. In the system there is a computer unit comprising means for determining a pantoscopic angle α' of the spectacle frame related to the position of the image plane, comprising means for correcting the pantoscopic angle α' of the spectacle frame in accordance with the acquired inclination angle γ of the image plane in relation to the vertical direction so as to form a pantoscopic angle α related to the vertical direction, comprising means for determining a head rotation angle β of the head of the subject, formed by the optical axis of the camera with a plane perpendicular to the distance line of the pupils of the eyes of the subject, and comprising means for correcting the head rotation angle β in accordance with the detected inclination angle γ of the image plane in relation to the vertical direction so as to form a corrected head rotation angle β' corresponding to a horizontal alignment of the optical axis of the camera. The computer unit contains means for determining an intersection of the viewing direction of the subject with the frame plane. The computer unit moreover has means for determining the distance visual point as the intersection of a virtual viewing direction lying in a horizontal plane with the frame plane, by means of which the virtual viewing direction is determined as the direction of a virtual straight line, which is established by rotating a straight line which is set by a reference point arranged on the eye with a known position in relation to the camera or the spectacle frame and the intersection of the viewing direction, by virtue of this straight line being, firstly, rotated at a virtual pivot, which lies at a distance from the reference point and on this straight line within the eye, about an axis lying parallel to the vertical direction by a first angle ($\beta_{OD}''$, $\beta_{OS}''$) dependent on the corrected head rotation angle ($\beta''$). Secondly, this straight line is rotated at the virtual pivot about a further axis by a further angle ($'''$) dependent on the corrected pantoscopic angle ($'$). This further axis is parallel to the distance line of the pupils of the eyes of the subject. If the eye is a right eye of the subject, the following applies for the first angle ($\beta_{OD}''$) which is dependent on the corrected head rotation angle ($\beta'$): $\tan \beta_{OD}''=(0.5 \times P_D \times \cos \beta' + YZ)/(D+HSA)$ and if the eye 62 is a left eye of the subject 68, the following applies: $\tan \beta_{OS}''=(0.5 \times P_D \times \cos \beta' - YZ)/(D+HSA)$. Here, $P_D$ is the interpupillary distance of the eyes of the subject. D+HSA is the vertical distance of the camera from a vertical plane, in which the distance line of the pupils of the eyes is situated. YZ is the offset of the intersection (Y) of the distance line of the pupils of the eyes with the vertical projection of the optical axis of the camera into a horizontal plane, in which the distance line of the pupils of the eyes is situated, from the intersection (Z) of the distance line of the pupils of the eyes with a vertical plane intersecting the distance line of the pupils of the eyes, the plane being perpendicular to the frame plane and the vertical axis of symmetry of the spectacle frame lying in the plane. The following applies for the further angle (α'') dependent on the corrected pantoscopic angle (α): $\alpha''=-(\gamma+\delta)$, where δ is the angle which the optical axis of the camera forms with the perpendicular projection of the viewing direction into a vertical plane, in which the optical axis of the camera lies.

The means for determining a pantoscopic angle α' of the spectacle frame related to the position of the image plane, the means for correcting the pantoscopic angle α' of the spectacle frame in accordance with the acquired inclination angle γ of the image plane in relation to the vertical direction so as to form a pantoscopic angle α related to the vertical direction and the means for determining a head rotation angle β of the head of the subject, formed by the optical axis of the camera with a plane perpendicular to the distance line of the pupils of the eyes of the subject, and also the means for correcting the head rotation angle β in accordance with the detected inclination angle γ of the image plane in relation to the vertical direction so as to form a corrected head rotation angle β' corresponding to a horizontal alignment of the optical axis of the camera and the means for determining the at least one fitting parameter by analyzing the image lying in the image plane, taking into account the corrected head rotation angle β' corresponding to a horizontal alignment of the optical axis of the camera can be embodied as a computer unit with a computer program loaded into the computer unit. A corresponding statement applies to the means for determining an intersection of the viewing direction of the subject with the frame plane and the means for determining the distance visual point.

The camera can be integrated into a tablet computer and/or a cellular telephone, wherein the computer unit is preferably embodied as a server connected to the tablet computer and/or the cellular telephone. In this way it is possible to ensure a short computational time for evaluating the acquired images.

By virtue of the tablet computer and/or the cellular telephone communicating wirelessly with the server, it is possible to record the images of a portion of a spectacle frame worn by a subject with the greatest possible freedom of movement.

The computer program according to the invention contains, in particular, program code for carrying out the method steps, specified below, in a method described above for determining a distance visual point and preferably also at least one fitting parameter for a spectacle lens which is receivable in a spectacle frame, when the computer program is executed in the computer unit of a system as described above:

acquiring an image, lying in an image plane, of at least one portion of a spectacle frame worn by a subject by a camera with an optical axis while the subject looks into the camera with a viewing direction of at least one eye passing through the frame plane;

establishing a pantoscopic angle α' of the spectacle frame related to the position of the image plane;

correcting this pantoscopic angle α' in accordance with the acquired inclination angle γ of the image plane in relation to the vertical direction so as to form a pantoscopic angle α related to the vertical direction;

establishing a head rotation angle β of the head of the subject, formed by the optical axis of the camera with a plane perpendicular to the distance line of the pupils of the eyes of the subject;

correcting the head rotation angle β in accordance with the detected inclination angle γ of the image plane in relation to the vertical direction so as to form a corrected head rotation angle β corresponding to a horizontal alignment of the optical axis of the camera;

determining the distance visual point by analyzing the image lying in the image plane, taking into account the corrected head rotation angle β corresponding to a horizontal alignment of the optical axis of the camera, as follows:

determining the intersection of the viewing direction with the frame plane by means of image evaluation; and, determining the distance visual point as the intersection of a virtual viewing direction lying in a horizontal plane with the frame plane, wherein the virtual viewing direction is determined as the direction of a virtual straight line, which is established by rotating a straight line which is set by a reference point arranged on the eye with a known position in relation to the camera or the spectacle frame and the intersection of the viewing direction, by virtue of this straight line being, firstly, rotated at a virtual pivot, which lies at a distance from the reference point and on this straight line within the eye, about an axis lying parallel to the vertical direction by a first angle ($β_{OD}"$, $β_{OS}"$) dependent on the corrected head rotation angle (β') and by virtue of, secondly, this straight line being rotated at the virtual pivot about a further axis parallel to the distance line of the pupils of the eyes of the subject by a further angle (α") dependent on the corrected pantoscopic angle (α).

If the eye 60 is a right eye of the subject 68, the following applies for the first angle ($β_{OD}$) which is dependent on the corrected head rotation angle (β'): $\tan β_{OD}" = (0.5 \times P_D \times \cos β' + YZ)/(D+HSA)$.

If the eye 62 is a left eye of the subject 68, the following applies for the first angle ($β_{OS}$) which is dependent on the corrected head rotation angle (β'): $\tan β_{OS}" = (0.5 \times P_D \times \cos β' - YZ)/(D+HSA)$.

Here, $P_D$ is the interpupillary distance of the eyes of the subject, D+HSA is the vertical distance of the camera from a vertical plane, in which the distance line of the pupils of the eyes is situated, and YZ is the offset of the intersection (Y) of the distance line of the pupils of the eyes with the vertical projection of the optical axis of the camera into a horizontal plane, in which the distance line of the pupils of the eyes is situated, from the intersection (Z) of the distance line of the pupils of the eyes with a vertical plane intersecting the distance line of the pupils of the eyes, the plane being perpendicular to the frame plane and the vertical axis of symmetry of the spectacle frame lying in the plane.

The following applies for the further angle (α") dependent on the corrected pantoscopic angle (α): α"=−(γ+δ), where δ is the angle which the optical axis of the camera forms with the perpendicular projection of the viewing direction into a vertical plane, in which the optical axis of the camera lies.

A computer program according to the invention can also contain program code for analyzing, by means of image evaluation, a recording of the subject from the side with at least three side target marks, which are fixed in relation to the spectacle frame and which define a further coordinate system, for the purposes of determining the vertex distance (HSA).

BRIEF DESCRIPTION OF THE DRAWINGS

The invention will now be described with reference to the drawings wherein:

FIG. 5A and FIG. 5B show views of front target marks of the measurement bracket in the case of a spectacle frame without pantoscopic tilt;

FIG. 6A and FIG. 6B show views of front target marks of the measurement bracket in the case of a spectacle frame with pantoscopic tilt; and, FIG. 7A and FIG. 7B show views of front target marks of the measurement bracket for a head position of the subject, in which he or she does not look into the camera.

DESCRIPTION OF THE PREFERRED EMBODIMENTS OF THE INVENTION

Figure 1:
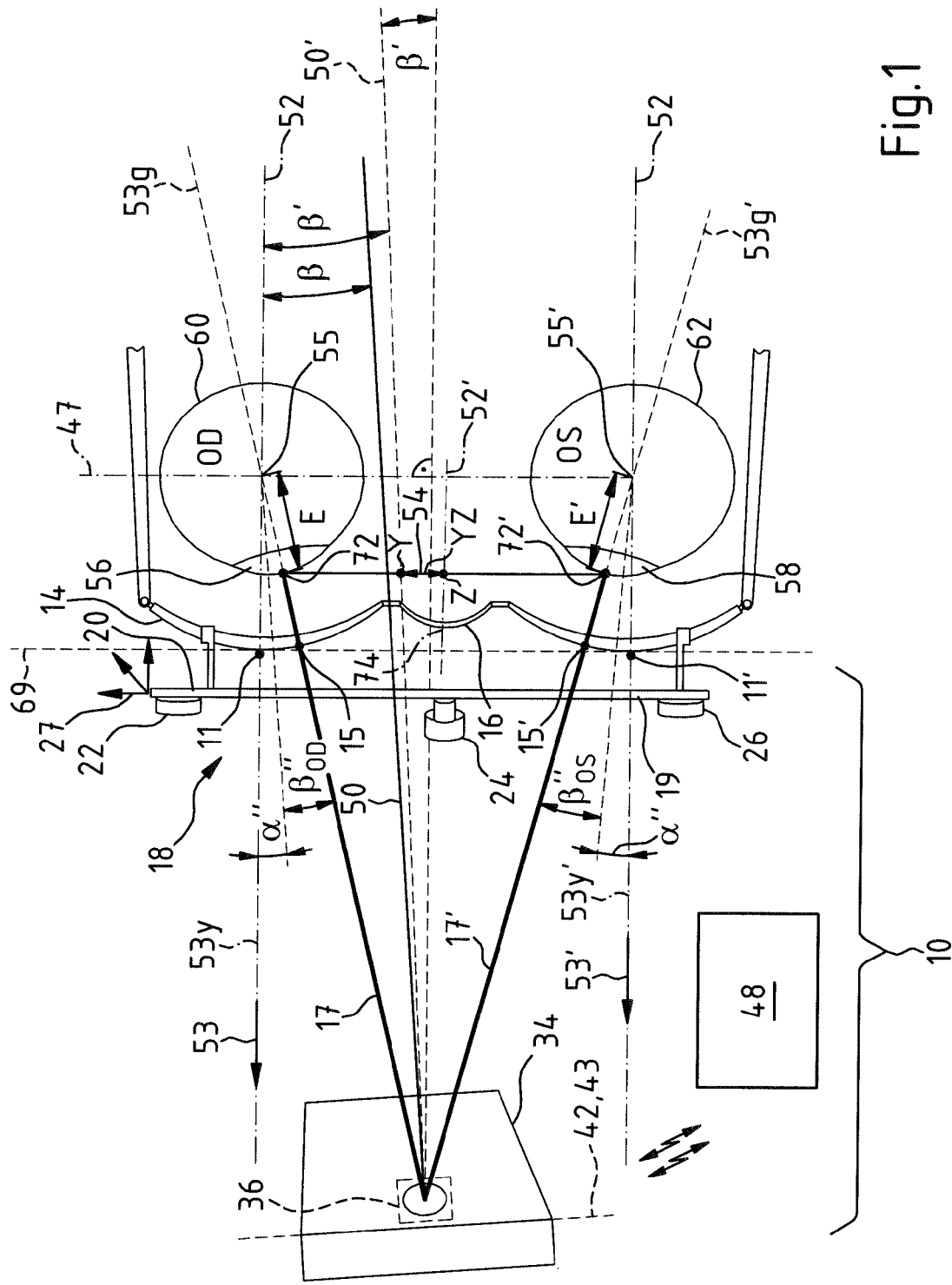
FIG. 1 shows a top plan view of a system for determining fitting parameters for a spectacle lens received in a spectacle frame with a measurement bracket and with a camera.

The system 10 shown in FIG. 1 allows a user to determine the far visual point (11, 11') defined in the standard EN ISO 13666 and further fitting parameters for a first spectacle lens 12 and a second spectacle lens 14, which are intended to be held in a spectacle frame 16 already adapted to the anatomy of a spectacle wearer. To this end, the system 10 contains a measurement bracket 18, which can be detachably fastened to the spectacle frame 16. By way of example, the measurement frame 18 can have the setup as described in U.S. Pat. No. 7,588,335, the entirety of which is referred to in this respect and the disclosure of which is incorporated herein by reference.

For the purposes of fitting to different frame geometries, the measurement bracket 18 has an adjustable traverse 20 and two adjustable limbs (not depicted here) which are mounted with pivotable movement. The measurement bracket 18 can be clamped to a spectacle frame 16 by means of frame receptacles arranged on the traverse 20 and the adjustable limbs.

At the front side 19 thereof, the measurement bracket 18 is provided with a left, a central and a right front target mark (22, 24, 26). The front target marks (22, 24, 26) are arranged in the region of the traverse 20. Here, the left and right front target marks (22, 26) are positioned set back in relation to the central front target mark 24. The front target marks (22, 24, 26) define a coordinate system 27 that is fixed in relation to the measurement bracket 18 and the spectacle frame 16 to which the measurement bracket 18 is connected.

Figure 2:
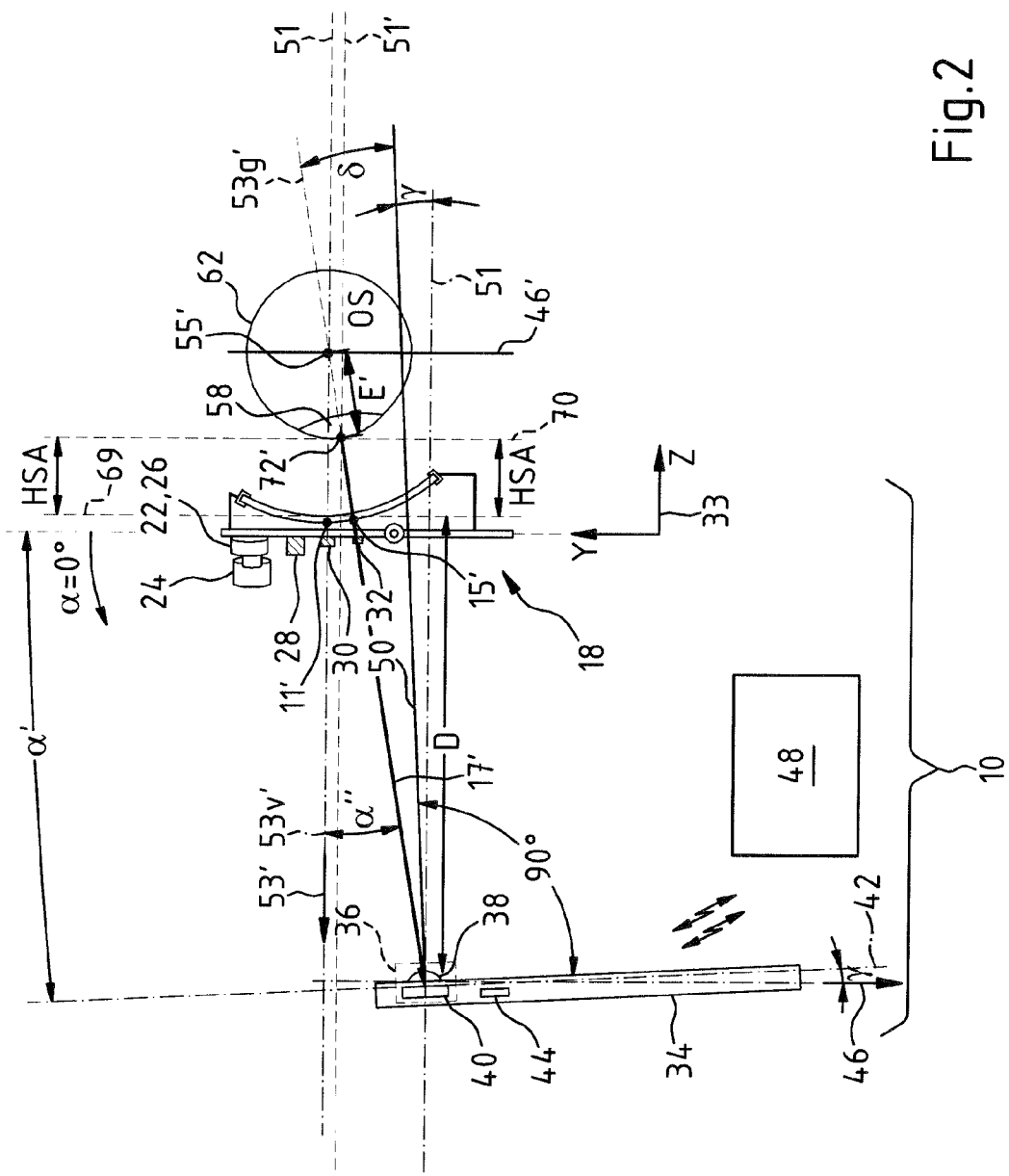
FIG. 2 shows the system for determining fitting parameters in a side elevation view.

FIG. 2 is a side elevation view of the system 10. In each case, the measurement bracket 18 has three side target marks (28, 30, 32) on the left-hand and right-hand side thereof. The side target marks are arranged between the two adjustable limbs and the traverse 20. The side target marks (28, 30, 32) define a further coordinate system 33 which is referenced to the coordinate system 27 of the measurement bracket 18 and of the spectacle frame 16. As shown in FIG. 2, the side target mark 28 of the measurement bracket 18 is positioned set back in the x-direction of the coordinate system 33 in relation to the side target marks (30, 32).

Figure 3:
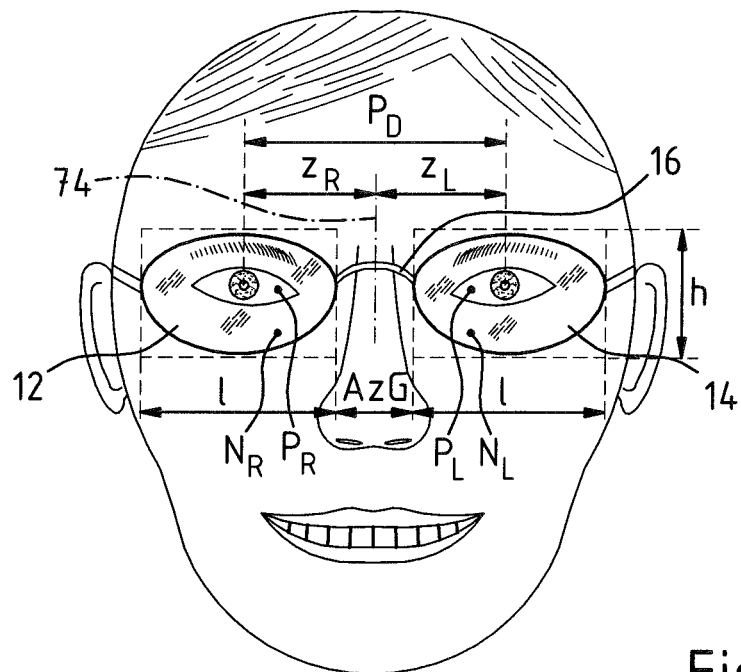
FIG. 3 shows a front view of a spectacle frame on a wearer thereof.
Figure 4:
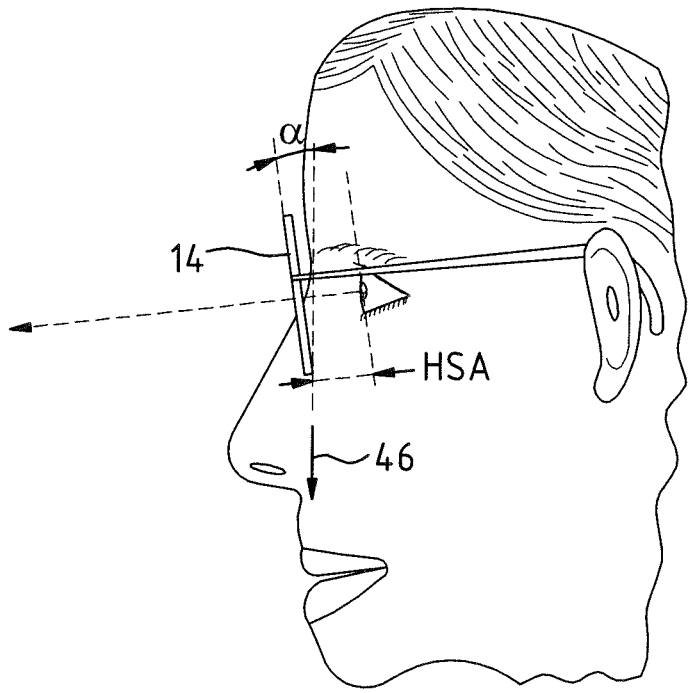
FIG. 4 shows a side view of a spectacle frame on a wearer thereof.

FIG. 3 is a front view of the frame plane and shows, therein, the vertical axis of symmetry 74 of the spectacle frame 16 and different fitting parameters for the spectacle lenses (12, 14) in the spectacle frame 16. FIG. 4 shows a side view of the spectacle frame with the eye of a subject or wearer.

For the purposes of determining the far visual point (11, 11') and further fitting parameters, a portion of the spectacle frame 16 worn by a subject 68 is acquired digitally in the system 10 shown in FIG. 1 and FIG. 2. To this end, the system 10 has a tablet computer 34 which contains a camera 36. The tablet computer 34 has a touch-sensitive image screen 38. The camera 36 has imaging optics 38 and contains an image sensor 40 which is arranged in a camera image plane 42.

The tablet computer 34 contains an inclination sensor 44, by means of which the angle γ of the inclination of the camera image plane 42 in relation to the direction 46 of gravity can be detected. The inclination sensor 44 renders it possible to detect the inclination of the camera image plane 42 in relation to the vertical direction 46 of gravity, that is, it renders it possible to determine the inclination of the camera image plane 42 about a horizontal axis 43 parallel to the camera image plane 42, when the camera 36 is used to record an image of the spectacle frame 16 worn by a subject 68 in the portion of the spectacle frame 16. The tablet computer 34 contains an application program (app) for the purposes of acquiring images with the associated angle γ of the inclination of the camera image plane 42.

The system 10 has a computer unit 48 embodied as a server computer. The computer unit 48 is wirelessly connected to the tablet computer 34 by means of WLAN transfer technology. For an image recorded with the camera 36 in the tablet computer 34, the computer unit 48 obtains the digital image data acquired by means of the image sensor 40 and the angle γ of the inclination of the camera image plane 42 in relation to the direction 46 of gravity.

The computer unit 48 contains a computer program for the purposes of determining the fitting parameters. The computer program has a computational algorithm by means of which the pantoscopic angle α, related to the direction 46 of gravity, of the spectacle frame 16 and the head rotation angle β in relation to the optical axis 50 of the camera 36 are established by digital image analysis, that is, by image evaluation, from an image of the portion of the spectacle frame 16 worn by the subject with the measurement bracket 18 connected thereto. The measurement bracket contains the three front target marks (22, 24, 26) arranged at the traverse 20 thereof. Thus, the head rotation angle β is that angle which the optical axis 50 of the camera 36 forms with a plane 52 which is perpendicular to the distance line 54 of the pupils (56, 58) of the eyes (60, 62) of the subject 68, that is, to an imaginary connecting line between the eyes (60, 62) of the subject 68.

Here, the pantoscopic angle α of the spectacle frame 16 and the head rotation angle β are calculated from the position of the front target marks (22, 24, 26) in the image plane 42 of the camera 36. What is employed here is the fact that the central front target mark 24 has the distance B from the plane in which the front target marks 22 and 26 of the measurement bracket 18 lie, as shown in FIG. 5A and FIG. 5B.

If the spectacle frame 16 with the measurement bracket 18 has a pantoscopic angle α=0° in relation to the vertical direction 46 and if γ=0 likewise applies to the inclination angle γ of the image plane 42 of the camera 36 in relation to the vertical direction 46, then what this achieves is that the camera 36 acquires the front target marks (22, 24, 26) as an image in which the marks lie on an imagined connecting line 66, as emerges from FIG. 5A. However, if the spectacle frame 16 is inclined in relation to the vertical direction 46, as shown in FIG. 5B, the image of the central front target mark 24 acquired by means of the camera 36 in the image plane 42 of the camera 36 is offset by a value A in relation to an imaginary connecting line 66 between the image of the front target mark 22 and the image of the front target mark 26, as can be seen in FIG. 6A. Therefore, the sought-after pantoscopic angle α can be established as α=arctan(A/B) from the known distance B of the front target mark 24 from the connecting line of the front target marks (22, 26).

If the image plane 42 of the camera 36 is inclined by a horizontal axis parallel to the image plane 42 corresponding to the angle γ, the computer program still corrects a pantoscopic angle α', established on the basis of the relationship described above, of the spectacle frame 16 in relation to the image plane 42 of the camera by the angle γ, detected by means of the inclination sensor 44, in relation to a pantoscopic angle α related to the vertical distance 46.

If the optical axis 50 of the camera 36 includes the head rotation angle β>0 with the plane 52, the image, detected by means of the camera 36, of the central front target mark 24 in the image plane 42 of the camera 36 is likewise displaced, in respect of the view of FIG. 7A, by a value C between the image of the front target mark 22 and the image of the front target mark 26, as can be seen in FIG. 7A and FIG. 7B. Here, β'=arctan(C/B(cos(α'−γ)) applies for the head rotation angle β' related to the vertical direction 46.

From the relative position, established by means of image evaluation, of the front target marks 22, 24 and 26 in the image plane 42 of the camera 36, the computer program in the computer unit 48 then calculates the head rotation angle β on the basis thereof.

If the image plane 42 of the camera 36 is inclined by a horizontal axis, parallel to the image plane 42, corresponding to the angle β, the computer program corrects the head rotation angle β established on the basis of the relationship described above in accordance with the angle γ detected by means of the inclination sensor 44 to form a corrected head rotation angle β', which corresponds to a horizontal alignment of the optical axis 50 of the camera. Thus, the corrected head rotation angle β' is the angle which the perpendicular projection 50', shown in FIG. 1, of the optical axis 50 of the camera 36 in one horizontal plane forms with the generally vertical plane 52 perpendicular to the distance line 54 of the pupils 56, 58 of the eyes (60, 62) of the subject 68.

Then, the computer program is used to convert the image of the portion of the spectacle frame 16 worn by the subject 68 with the measurement bracket 18 connected thereto, the measurement bracket containing the three front target marks (22, 24, 26) arranged on the traverse 20 thereof, into an image data record which is corrected in accordance with the angle γ of the inclination of the image plane 42 of the camera 36 about the horizontal axis 43 and the corrected head rotation angle β' corresponding to a horizontal alignment of the optical axis 50 of the camera such that this image data record then corresponds to a camera image in which the subject looks into the camera 36 and the image plane 42 of the camera 36 is aligned precisely vertically. In this conversion, the computer program takes into account the different distances of the measurement bracket 18, of the spectacle frame 16 and of the pupils (56, 58) of the eyes (60, 62) of the subject from the camera 36 as follows:

By means of image evaluation, the computer program determines the intersection 15 or 15' of the viewing direction 17 or 17' of the right and left eye 60 or 62 of the subject 68, shown in FIG. 1, with the frame plane 69 of the spectacle frame 16. The distance visual point 11 or 11' is determined as the intersection of a virtual viewing direction (53, 53') lying in a horizontal plane 51 with the frame plane 69.

Here, the virtual viewing direction 53 or 53' is determined as the direction of a virtual straight line 53v or 53v', which emerges from a straight line 53g or 53g' by rotation about a virtual pivot 55 or 55'. The straight line 53g or 53g' corresponds to the viewing direction of the right or left eye (60, 62) of the subject. The straight line 53g or 53g' is set by a reference point 72 or 72', arranged on the eye (60, 62), with a known position in relation to the camera 36 or the spectacle frame 16 and the intersection 15 or 15' of the viewing direction 17 or 17'. In order to convert a straight line 53g or 53g' into the virtual straight line 53v or 53v', the straight line 53g or 53g' is, firstly, rotated at a virtual pivot (55, 55'), which lies at a distance from the reference point 72 or 72' and on the straight line 53g or 53'g within the eye (60, 62), about an axis 46' lying parallel to the vertical direction 46 by a first angle $\beta_{OD}"$ or $\beta_{OS}"$ dependent on the corrected head rotation angle β'. The virtual pivot 55 or 55' lies on the straight line 53g or 53g' and has the predetermined distance E or E', visible in FIG. 1, from the reference point 72 or 72'. By way of example, E=E'=15.5 mm or E=E'=12.5 mm applies for the distance E and the distance E'.

Secondly, the straight line 53g or 53'g is rotated at the virtual pivot 55 or 55' about a further axis parallel to the distance line of the pupils of the eyes of the subject by a further angle (α") dependent on the corrected pantoscopic angle (α). Here, if the eye 60 is a right eye of the subject 68, the following applies for the first angle ($\beta_{OD}"$) which is dependent on the corrected head rotation angle (β'): tan $\beta_{OD}"=(0.5 \times P_D \times \cos \beta' + YZ)/(D+HSA)$. If the eye 62 is a left eye of the subject 68, the following applies for the first angle ($\beta_{OS}"$) which is dependent on the corrected head rotation angle (β'): tan $\beta_{OS}"=(0.5 \times P_D \times \cos \beta' - YZ)/(+HSA)$. $P_D$ is the interpupillary distance of the eyes of the subject 68 and D+HSA is the vertical distance of the camera 36 from the vertical plane 70, in which the distance line 54 of the pupils of the eyes 60 or 62 is situated. YZ is the offset of the intersection (Y) of the distance line 54 of the pupils (56, 58) of the eyes (60, 62) with the vertical projection 50' of the optical axis 50 of the camera 36 into a horizontal plane 51', in which the distance line 54 of the pupils (56, 58) of the eyes (60, 62) is situated, from the intersection (Z) of the distance line 54 of the pupils (56, 58) of the eyes (60, 62) with a vertical plane 52' intersecting the distance line 54 of the pupils (56, 58) of the eyes (60, 62), the plane being perpendicular to the frame plane 69 and the vertical axis of symmetry 74 of the spectacle frame 16 lying in the plane. Here, the following applies for the further angle (α") dependent on the corrected pantoscopic angle (α): α"=−(γ+δ). δ is the angle which the optical axis 50 of the camera 36 forms with the perpendicular projection of the viewing direction (17, 17') into a vertical plane, in which the optical axis 50 of the camera 36 lies.

For the purposes of determining the distance visual point, the computer program preferably takes into account the position of the measurement bracket 18 in relation to the frame plane 69 of the spectacle frame 16 shown in FIG. 1 and in FIG. 2, which frame plane, as described in U.S. Pat. No. 7,588,335, is structurally predetermined and therefore known. Moreover, the computer program preferably takes into account a vertex distance HSA, defined pursuant to the standard EN ISO 13666:2012, as a known position of a reference point (72, 72'), fixed in relation to the subject 68, in the coordinate system 27 defined by means of the three front target marks (22, 24, 26), fixed in relation to the spectacle frame 16, or in a coordinate system (not shown here) referenced to the spectacle frame 16 or the camera 36. To this end, the vertex distance HSA can be read, for example, from a database and fed to the computer program. In particular, it can correspond to a mean value of various subjects 68, for example, to a mean value of a certain population of subjects or certain sub-groups of a population of subjects. As an alternative thereto, provision can also be made for the computer program to contain the vertex distance (HSA) which is determined in a preceding measurement by means of a PD ruler or by analyzing a recording of the subject 68, from the side by means of image evaluation, with the measurement bracket 18 fastened to the spectacle frame 16. As a result, the computer program takes into account parallax errors in the image of the subject 68 acquired by means of the camera 36 for the purposes of determining the distance visual point (11, 11'), the cause of the parallax errors being a finite distance between the eyes (60, 62) of the subject 68 and the frame plane 69 of the spectacle frame 16. What this achieves is that the precise head position of the subject 68 in relation to the camera 36 can be deduced from the image of points, arranged on the measurement bracket 18 and the spectacle frame 16, in the image plane 42 of the camera 36 and from the image of reference points (72, 72') arranged on the subject 68 in the image plane 42 of the camera 36.

It should be noted that the reference point (72, 72') can also be defined as the center of the pupil of the eye (60, 62) of the subject 68, which is established by means of image evaluation or individually set by an optician in an image containing the eyes (60, 62) of the subject 68.

Determining fitting parameters is then carried out from the distance visual point and from the acquired image by means of image evaluation.

For the purposes of determining fitting parameters for a subject 68, a user of the system 10 has a great degree of freedom when acquiring images of the portion of the spectacle frame 16, worn by the subject 68, with a measurement bracket 18 assembled on the spectacle frame 16. This is because, in the method according to the invention for determining at least one fitting parameter for a spectacle lens which is receivable in a spectacle frame, it is not necessary for the direction of the optical axis 50 of the imaging optics 38 of the camera 36 of the tablet computer 34 to point to the head of the subject 68. In particular, the inventors could show that the accuracy for the detection of spectacle lens fitting parameters in the system 10 is not impaired, even if the following applies to the inclination angle γ from the vertical direction 46 of the image plane 42 of the camera 36 in the tablet computer 34: −20°≤γ≤20°.

It should be noted that, in an alternative embodiment of the invention, provision can be made for the pantoscopic angle α of the spectacle frame 16 in relation to the image plane 42 of the camera 36 and the head rotation angle β to be established only by means of image evaluation of an image of the spectacle frame 16, without a measurement bracket 18 with front target marks (22, 24, 26) being applied to the spectacle frame 16, by virtue of a known geometry of the spectacle frame 16 being taken into account in the image evaluation.

In the system 10, the visual points for distance can also be determined as fitting parameters, taking into account the inclination angle γ. It is possible to determine the distance visual point $P_{R/L}$ (right/left centration point) from the point through which the subject looks at the camera in an acquired image. It is likewise possible to determine a near visual point $N_{R/L}$ (right/left near visual point) which, together with the distance visual point $P_{R/L}$, defines a progressive lens. In addition to the near visual points $N_{R/L}$, it is also possible to determine the angle ε between the viewing direction of the eye (60, 62) of a subject 68 when looking into the distance and the viewing direction when looking close-by, for example, when reading. In particular, for the purposes of determining a fitting parameter, the system 10 does not require a reading situation to be acquired by an additional, further camera or together with an additional further camera and subsequently be evaluated.

Since the computer program of the computer unit 48 of system 10, as described above, takes into account the vertex distance HSA, defined pursuant to the standard EN ISO 13666:2012, as a known position of a reference point (72, 72') fixed in relation to the subject 68 in the coordinate system 27 defined by means of the three front target marks (22, 24, 26) fixed in relation to the spectacle frame 16, it is possible to identify—when determining the near visual points by means of the system 10 when the subject 68 assumes his habitual head position by looking straight into the camera 36 and, as a consequence thereof, holds his head with a slight twist in accordance with his leading eye—that the actual position of the near visual points deviates from a symmetrically nasally displaced position.

The computational algorithm of the computer program in the computer unit 48 of the system 10 is configured in such a way that, using it, it is not only possible to determine the pantoscopic angle α of the spectacle frame (pantoscopic tilt), but, alternatively or additionally, also the frame dimensions (I, h, AzG [distance between lenses]), the interpupillary distance (PD, $z_R$, $z_L$), the centration distance ($x_R$, $y_R$, $x_L$, $y_L$), the face form angle and the required lens blank diameter. The computer program can determine the vertex distance (HSA) in the computer unit 48 from a recording of the subject 68 from the side, when the latter wears the spectacle frame 16 with the measurement bracket 18 fixed thereon.

In summary, the following preferred features of the invention, in particular, should be registered: In a method for determining a distance visual point on a spectacle lens (12, 14) which is receivable in a spectacle frame 16 and which has a frame plane 69, an image, lying in an image plane 42, of at least one portion of a spectacle frame 16 worn by a subject 68 is acquired by a camera 36 with an optical axis 50 while the subject 68 looks into the camera 36 with a viewing direction (17, 17') of at least one eye (60, 62) passing through the frame plane 69. In so doing, a pantoscopic angle α' of the spectacle frame 16 related to the position of the image plane 42 is established. The pantoscopic angle α' is corrected in accordance with the acquired inclination angle γ of the image plane 42 in relation to the vertical direction 46 so as to form a pantoscopic angle α related to the vertical direction 46. A head rotation angle β of the head of the subject 68, formed by the optical axis 50 of the camera 36 with a plane perpendicular to the distance line 54 of the pupils (56, 58) of the eyes (60, 62) of the subject 68, is established and the head rotation angle β is corrected in accordance with the detected inclination angle γ of the image plane 42 in relation to the vertical direction 46 so as to form a corrected head rotation angle corresponding to a horizontal alignment of the optical axis 50 of the camera 36. The intersection 15' of the viewing direction (17, 17') with the frame plane 69 is then determined by means of image evaluation and, from this, the distance visual point (11, 11') is determined as the intersection of a virtual viewing direction (53, 53') lying in a horizontal plane 51 with the frame plane 69. The virtual viewing direction (53, 53') is determined as the direction of a virtual straight line (53v, 53v'), which is established by rotating a straight line (53g, 53'g) which is set by a reference point (72, 72') arranged on the eye (60, 62) with a known position in relation to the camera 36 or the spectacle frame 16 and the intersection (15, 15') of the viewing direction (17, 17'). To this end, this straight line (53g, 53'g) is, firstly, rotated at a virtual pivot (55, 55'), which lies at a distance from the reference point (72, 72') and on this straight line (53g, 53g') within the eye (60, 62), about an axis 46' lying parallel to the vertical direction 46 by a first angle $β_{OD}"$, $β_{OS}"$ dependent on the corrected head rotation angle (β'). Secondly, this straight line (53g, 53g') is rotated at the virtual pivot (55, 55') about a further axis 47 parallel to the distance line 54 of the pupils (56, 58) of the eyes (60, 62) of the subject 68 by a further angle (α") dependent on the corrected pantoscopic angle (α). If the eye 60 is a right eye of the subject 68, the following applies for the first angle $β_{OD}"$ which is dependent on the corrected head rotation angle (β'): $\tan β_{OD}"=(0.5×P_D×\cos β+YZ)/(D+HSA)$. If the eye 62 is a left eye of the subject 68, the following applies for the first angle $β_{OS}"$ which is dependent on the corrected head rotation angle (β'): $\tan β_{OS}"=(0.5×P_D×\cos β'-YZ)/(D+HSA)$. Here, $P_D$ is the interpupillary distance of the eyes of the subject 68. D+HSA is the vertical distance of the camera 36 from a vertical plane 70, in which the distance line 54 of the pupils of the eyes (60, 62) is situated. YZ is the offset of the intersection (Y) of the distance line 54 of the pupils (56, 58) of the eyes (60, 62) with the vertical projection 50' of the optical axis 50 of the camera 36 into a horizontal plane 51', in which the distance line 54 of the pupils (56, 58) of the eyes (60, 62) is situated, from the intersection (Z) of the distance line 54 of the pupils (56, 58) of the eyes (60, 62) with a vertical plane 52' intersecting the distance line 54 of the pupils (56, 58) of the eyes (60, 62), the plane being perpendicular to the frame plane 69 and the vertical axis of symmetry 74 of the spectacle frame 16 lying in the plane. The following applies for the further angle α" dependent on the corrected pantoscopic angle (α): α"=−(γ+δ), where δ is the angle which the optical axis 50 of the camera 36 forms with the perpendicular projection of the viewing direction (17, 17') into a vertical plane, in which the optical axis 50 of the camera 36 lies.

It is understood that the foregoing description is that of the preferred embodiments of the invention and that various changes and modifications may be made thereto without departing from the spirit and scope of the invention as defined in the appended claims.

LIST OF REFERENCE SIGNS

10 System
11, 11' Far visual point
12, 14 Spectacle lens
15, 15' Intersection or intercept
16 Spectacle frame
17, 17' Viewing direction
18 Measurement bracket
19 Front side
20 Traverse
22, 24, 26 Front target mark
27 Coordinate system
28, 30, 32 Side target marks
33 Coordinate system
34 Tablet computer 36 Camera
38 Imaging optics/image screen
40 Image sensor
42 Image plane
43 Horizontal axis
44 Inclination sensor
46 Vertical direction
46' Axis parallel to the vertical direction
47 Axis perpendicular to the axis 46' and the plane 52
48 Computer unit
50 Optical axis
50' Projection of the optical axis
51, 51' Horizontal plane
52 Vertical plane
52' Vertical plane through the axis of symmetry of the spectacle frame
53, 53' Virtual viewing direction
53g, 53g' Straight line
53v, 53v' Virtual straight line through the virtual pivot of an eye
54 Distance line of the pupils
55, 55' Virtual pivot
56, 58 Pupils
60, 62 Eyes
66 Connecting line
68 Subject
69 Frame plane
70 Vertical plane
72, 72' Reference point
74 Vertical axis of symmetry of the spectacle frame
60 Pantoscopic angle related to the vertical direction
$\alpha'$ Pantoscopic angle related to the camera image plane
$\alpha''$ Rotation angle
$\beta$ Head rotation angle
$\beta'$ Corrected head rotation angle
$\beta_{OS}''$ Rotation angle
$\gamma$ Angle of inclination of the camera image plane in relation to the vertical
A, B, C, D Distance
HAS Vertex distance
E, E' Distance between virtual pivot and reference point on the left and right eye, respectively
$P_D$ Interpupillary distance of the eyes of the subject
Y, Z Point
YZ Distance of the point Y from the point Z

What is claimed is:
1. A method for determining a far vision point on a spectacle lens mountable in a spectacle frame defining a frame plane, the method comprising the steps of:
providing a camera defining an optical axis;
capturing an image of at least one section of the spectacle frame worn by a subject with the camera wherein the image lies in an image plane and includes pupils of eyes of the subject and while the subject looks in a viewing direction passing through the frame plane with at least one eye into the camera wherein the viewing direction and the frame plane conjointly define an intercept;
determining a pantoscopic angle $\alpha'$ of the spectacle frame referred to the position of said image plane;
capturing an inclination angle $\gamma$ of said image plane relative to a vertical direction;
correcting said pantoscopic angle $\alpha'$ to a pantoscopic angle $\alpha$ referred to said vertical direction in correspondence to said captured inclination angle $\gamma$;
determining a head rotation angle $\beta$ of the head of the subject conjointly defined by the optical axis of the camera and a plane perpendicular to the distance line of the pupils of the eyes of the subject;
correcting the head rotation angle $\beta$ in correspondence to the captured inclination angle $\gamma$ of the image plane relative to the vertical direction to a head rotation angle $\beta'$ corrected in correspondence to a horizontal alignment of the optical axis of the camera;
determining the far vision point by analyzing the image lying in the image plane while considering the head rotation angle $\beta'$ corrected in correspondence to the horizontal alignment of the optical axis of the camera;
determining said intercept of the viewing direction and the frame plane via image evaluation;
determining the far vision point as an intercept of a virtual viewing direction and the frame plane wherein the virtual viewing direction lies in a horizontal plane;
determining the virtual viewing direction as the direction of a virtual straight line which is detected by rotating a further straight line defined by a reference point arranged on the eye wherein the reference point has a known position with reference to the camera or the spectacle frame and the intercept of the viewing direction;
in that, said further straight line is rotated in a virtual pivot about a first angle $\beta_{OD}''$, $\beta_{OS}''$, which is dependent upon the corrected head rotation angle $\beta'$, about an axis parallel to the vertical direction and wherein the virtual pivot is spaced from the reference point and lies within the eye on the further straight line; and,
in that, the further straight line is rotated in said virtual pivot about a further axis by a further angle $\alpha''$, wherein the further axis is parallel to the distance line of the pupils of the eyes of the subject and the further angle $\alpha''$ is dependent upon the corrected pantoscopic angle $\alpha$;
wherein the following applies for the first angle $\beta_{OD}''$ when the eye is a right eye of the subject:

$\tan \beta_{OD}''=(0.5\times P_D\times\cos \beta'+YZ)/(D+HSA)$ said first angle $\beta_{OD}''$ being dependent upon the corrected head rotation angle $\beta'$;
wherein the following applies for the first angle $\beta_{OS}''$ when the eye is a left eye of the subject:

$\tan \beta_{OS}''=(0.5\times P_D\times\cos \beta'-YZ)/(D+HSA)$ said first angle $\beta_{OS}''$ being dependent upon the corrected head rotation angle $\beta'$;
in the above:
$P_D$ is the interpupillary distance of the eyes of the subject; and,
(D+HSA) is the perpendicular distance of the camera from a vertical plane wherein the distance line of the pupils of the eyes lies;
YZ is the distances between the intercept Y of the distance line of the pupils of the eyes with the perpendicular projection of the optical axis of the camera in a horizontal plane wherein the distance lines of the pupils of the eyes are located and the intercept Z of the distance line of the pupils of the eyes with a vertical plane which intersects the distance line of the pupils of the eyes and is perpendicular to the frame plane and wherein the vertical symmetry axis of the spectacle frame lies;
for the further angle $\alpha''$, the following applies:

$\alpha''=-(\gamma+\delta)$ wherein the further angle is dependent from the corrected pantoscopic angle $\alpha$; and, wherein δ is the angle conjointly defined by the optical axis of the camera and the perpendicular projection of the viewing direction in a vertical plane wherein the optical axis of the camera lies.

2. The method of claim 1, wherein:

the pantoscopic angle α' of the spectacle frame is determined via image analysis of the captured image of at least one section of the spectacle frame wherein the pantoscopic angle α is referred to the position of the image plane and the spectacle frame is worn by the subject; and/or, the head rotation angle β of the head of the subject is determined via an image analysis of the captured image of the at least one section of the spectacle frame worn by the subject and wherein the head rotation angle β is conjointly defined by the optical axis of the camera and a plane perpendicular to the distance line of the pupils of the eyes of the subject.

3. The method of claim 1, wherein the corrected pantoscopic angle α satisfies the following relationship: α=α'−γ.

4. The method of claim 1, wherein the corrected head rotation angle β' satisfies the following relationship: β'=β/cos (α'−γ).

5. The method of claim 1, wherein the reference point is the corneal vertex of the eye of the subject and/or the reference point is a fixed center of the pupil of the eye of the subject.

6. The method of claim 1, wherein the position of the virtual pivot on the further straight line is determined by specifying a fixed distance of the virtual pivot from the reference point wherein the further straight line is determined by the reference point of the known position with reference to the camera or spectacle frame and the intercept of the viewing direction.

7. The method of claim 1, wherein the interpupillary distance $P_D$ of the eyes of the subject is determined via image analysis of an image captured by the camera wherein the captured image holds the pupils of the eyes of the subject and at least one section of the spectacle frame worn by the subject.

8. The method of claim 1, wherein the angle δ is conjointly defined by the optical axis of the camera and the perpendicular projection of the viewing direction in a vertical plane; and, the angle δ is determined via image analysis of the captured image of the at least one section of the spectacle frame worn by the subject.

9. The method of claim 1, wherein said distance YZ is determined via image analysis of said image captured by the camera.

10. The method of claim 1, wherein the determination of a far vision point and the determination of an adaptation parameter from the determined far vision point and from additional information obtained from the captured image is obtained via image analysis.

11. A system for determining a far vision point on a spectacle lens mountable in a spectacle frame defining a frame plane, the system comprising:

a camera having an image plane and including an inclination sensor configured to detect the inclination of said image plane about a horizontal axis;

a computer unit including:

first means for determining a pantoscopic angle α of said spectacle frame with said pantoscopic angle α' being referenced to the position of said image plane;

second means for correcting said pantoscopic angle α' of said spectacle frame to a pantoscopic angle α referred to a vertical direction in correspondence to a captured inclination angle γ of the image plane relative to said vertical direction;

third means for determining a head rotation angle β of the head of a subject wherein said head rotation angle β is conjointly defined by an optical axis of the camera and a plane perpendicular to the distance line of the pupils of the eyes of the subject;

fourth means for correcting said head rotation angle β to a head rotation angle β' in correspondence to the captured inclination angle γ of said image plane relative to said vertical direction and said head rotation angle β' being corrected in correspondence to a horizontal alignment of said optical axis of said camera;

fifth means for determining an intercept of the viewing direction of the subject and the frame plane;

sixth means for determining the far vision point as an intercept of a virtual viewing direction and the frame plane wherein the virtual viewing direction lies in a horizontal plane;

said computer unit being configured to determine said virtual viewing direction as the direction of a virtual straight line which is detected by rotating a further straight line defined by a reference point arranged on the eye wherein the reference point has a known position with reference to the camera or the spectacle frame and the intercept of the viewing direction;

in that, said further straight line is rotated in a virtual pivot about a first angle $β_{OD}"$, $β_{OS}"$, which is dependent upon the corrected head rotation angle β', about an axis parallel to the vertical direction and wherein the virtual pivot is spaced from the reference point and lies within the eye on the further straight line; and, in that, the further straight line is rotated in said virtual pivot about a further axis by a further angle α", wherein the further axis is parallel to the distance line of the pupils of the eyes of the subject and the further angle α" is dependent upon the corrected pantoscopic angle α;

wherein the following applies for the first angle $β_{OD}"$ when the eye is a right eye of the subject:

$$\tan β_{OD}" = (0.5 \times P_D \times \cos β' + YZ)/(D+HSA)$$

said first angle $β_{OD}"$ being dependent upon the corrected head rotation angle β';

wherein the following applies for the first angle $β_{OS}"$ when the eye is a left eye of the subject:

$$\tan β_{OS}" = (0.5 \times P_D \times \cos β' - YZ)/(D+HSA)$$

said first angle $β_{OS}"$ being dependent upon the corrected head rotation angle β';

in the above:

$P_D$ is the interpupillary distance of the eyes of the subject; and, (D+HSA) is the perpendicular distance of the camera from a vertical plane wherein the distance line of the pupils of the eyes lies;

YZ is the distances between the intercept Y of the distance line of the pupils of the eyes with a perpendicular projection of the optical axis of the camera in a horizontal plane wherein the distance lines of the pupils of the eyes are located and the intercept Z of the distance line of the pupils of the eyes with a vertical plane which intersects the distance line of the pupils of the eyes and is perpendicular to the frame plane and wherein a vertical symmetry axis of the spectacle frame lies;

for the further angle α", the following applies:

$$\alpha''=-(\gamma+\delta)$$

wherein the further angle is dependent from the corrected pantoscopic angle α; and, wherein δ is the angle conjointly defined by the optical axis of the camera and the perpendicular projection of the viewing direction in a vertical plane wherein the optical axis of the camera lies.

12. The system of claim 11 further comprising seventh means for determining at least one adaptation parameter from said far vision point and from a captured image via image evaluation.

13. The system of claim 11 further comprising a tablet computer or a mobile telephone with said camera being incorporated therein; and, said computer unit being configured as a server operatively connected to a corresponding one of said tablet computer and said mobile telephone.

14. The system of claim 13, wherein said at least one of said tablet computer and said mobile telephone is configured to communicate wirelessly with said server.

15. A computer program having a program code to perform all of the method steps of the method of claim 1 wherein the computer program is loaded into a computer or is carried out in a computer.

16. A program code stored on a non-transitory computer-readable medium, the program code being for determining, with a camera defining an optical axis, a far vision point on a spectacle lens mountable in a spectacle frame defining a frame plane, said program code being configured to, when executed by a processor, capture an image of at least one section of the spectacle frame worn by a subject with the camera wherein the image lies in an image plane and includes pupils of eyes of the subject and while the subject looks in a viewing direction passing through the frame plane with at least one eye into the camera wherein the viewing direction and the frame plane conjointly define an intercept;

determine a pantoscopic angle α' of the spectacle frame referred to the position of said image plane;

capture an inclination angle γ of said image plane relative to a vertical direction;

correct said pantoscopic angle α' to a pantoscopic angle α referred to said vertical direction in correspondence to said captured inclination angle γ;

determine a head rotation angle β of the head of the subject conjointly defined by the optical axis of the camera and a plane perpendicular to the distance line of the pupils of the eyes of the subject;

correct the head rotation angle β in correspondence to the captured inclination angle γ of the image plane relative to the vertical direction to a head rotation angle β' corrected in correspondence to a horizontal alignment of the optical axis of the camera;

determine the far vision point by analyzing the image lying in the image plane while considering the head rotation angle β' corrected in correspondence to the horizontal alignment of the optical axis of the camera;

determine said intercept of the viewing direction and the frame plane via image evaluation;

determine the far vision point as the intercept of a virtual viewing direction and the frame plane wherein the virtual viewing direction lies in a horizontal plane;

determine the virtual viewing direction as the direction of a virtual straight line which is detected by rotating a further straight line defined by a reference point arranged on the eye wherein the reference point has a known position with reference to the camera or the spectacle frame and the intercept of the viewing direction;

in that said further straight line is rotated in a virtual pivot about a first angle $\beta_{OD}''$, $\beta_{OS}''$, which is dependent upon the corrected head rotation angle β', about an axis parallel to the vertical direction and wherein the virtual pivot is spaced from the reference point and lies within the eye on the further straight line; and, in that the further straight line is rotated in said virtual pivot about a further axis by a further angle α", wherein the further axis is parallel to the distance line of the pupils of the eyes of the subject and the further angle α" is dependent upon the corrected pantoscopic angle α;

wherein the following applies for the first angle $\beta_{OD}''$ when the eye is a right eye of the subject:

$$\tan \beta_{OD}''=(0.5 \times P_D \times \cos \beta' + YZ)/(D+HSA)$$

said first angle $\beta_{OD}''$ being dependent upon the corrected head rotation angle β';

wherein the following applies for the first angle $\beta_{OD}''$ when the eye is a left eye of the subject:

$$\tan \beta_{OS}''=(0.5 \times P_D \times \cos \beta' - YZ)/(D+HSA)$$

said first angle $\beta_{OS}''$ being dependent upon the corrected head rotation angle β';

in the above:

$P_D$ is the interpupillary distance of the eyes of the subject; and, (D+HSA) is the perpendicular distance of the camera from a vertical plane wherein the distance line of the pupils of the eyes lies;

YZ is the distances between the intercept Y of the distance line of the pupils of the eyes with the perpendicular projection of the optical axis of the camera in a horizontal plane wherein the distance lines of the pupils of the eyes are located and the intercept Z of the distance line of the pupils of the eyes with the vertical plane which intersects the distance line of the pupils of the eyes and is perpendicular to the frame plane and wherein a vertical symmetry axis of the spectacle frame lies;

for the further angle α", the following applies:

$$\alpha''=-(\gamma+\delta)$$

wherein the further angle is dependent from the corrected pantoscopic angle α; and, wherein δ is the angle conjointly defined by the optical axis of the camera and the perpendicular projection of the viewing direction in a vertical plane wherein the optical axis of the camera lies.

* * * * *

UNITED STATES PATENT AND TRADEMARK OFFICE
CERTIFICATE OF CORRECTION

PATENT NO. : 9,971,172 B2
APPLICATION NO. : 15/274151
DATED : May 15, 2018
INVENTOR(S) : J. Cabeza-Guillen et al.

It is certified that error appears in the above-identified patent and that said Letters Patent is hereby corrected as shown below:

In the Specification

In Column 3:
Line 42: delete "angle $\alpha$" and insert -- angle $\alpha'$ -- therefor.

In Column 4:
Line 36: delete "tan $\beta_{OD}\theta$= (0.5×$P_D$×cos$\beta'$ +YZ)/D$\alpha$HSA)," and insert -- tan $\beta_{OD}''$ = (0.5×$P_D$×cos$\beta'$ +YZ)/D+HSA), -- therefor.

In Column 5:
Line 45: delete "$\alpha=\alpha'\gamma$" and insert -- $\alpha=\alpha'-\gamma$ -- therefor.
Line 46: delete "$\beta=\beta/\cos(\alpha'-\gamma)$" and insert -- $\beta'=\beta/\cos(\alpha'-\gamma)$ -- therefor.

In Column 7:
Line 55: delete "($\beta''$)" and insert -- ($\beta$) -- therefor.
Line 56: delete "($'''$)" and insert -- ($\alpha''$) -- therefor.
Line 57: delete "($'$)" and insert -- ($\alpha$) -- therefor.

In Column 9:
Line 12: delete "angle $\beta$" and insert -- angle $\beta'$ -- therefor.
Line 40: delete "($\beta_{OD}$)" and insert -- ($\beta_{OD}''$) -- therefor.

In Column 16:
Line 22: delete "tan $\beta_{OD}''$ = (0.5×$P_D$×cos$\beta$+YZ)/D+HSA)" and insert -- tan $\beta_{OD}''$ = (0.5×$P_D$×cos$\beta'$+YZ)/D+HSA) -- therefor.

In Column 17:
Line 31: delete "60" and insert -- $\alpha$ -- therefor.

Signed and Sealed this
Second Day of October, 2018

Andrei Iancu
*Director of the United States Patent and Trademark Office*

CERTIFICATE OF CORRECTION (continued)
U.S. Pat. No. 9,971,172 B2

In the Claims

<u>In Column 22</u>:
Line 11: add -- , -- after "in that".
Line 18: add -- , -- after "in that".
Line 29: delete "angle $\beta_{OD}'''$" and insert -- angle $\beta_{OS}''$ -- therefor.